(12) United States Patent
Jacques

(10) Patent No.: US 6,177,984 B1
(45) Date of Patent: *Jan. 23, 2001

(54) VIDEO IMAGING OF SUPERFICIAL BIOLOGICAL TISSUE LAYERS USING POLARIZED LIGHT

(75) Inventor: Steven Louis Jacques, Portland, OR (US)

(73) Assignee: Providence Health System, Portland, OR (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/012,886

(22) Filed: Jan. 23, 1998

(51) Int. Cl.[7] .................................................... G01N 33/48
(52) U.S. Cl. ........................... 356/39; 356/364; 356/338; 600/322
(58) Field of Search .................................... 356/364–369, 356/39, 445, 446, 338, 317, 318; 250/225; 382/133, 6, 134; 600/477, 478, 476, 475, 479, 473, 310, 315

(56) References Cited

U.S. PATENT DOCUMENTS

| | | | |
|---|---|---|---|
| 4,890,926 | * | 1/1990 | Dosmann et al. .................... 356/446 |
| 4,953,980 | * | 9/1990 | De Volk et al. ...................... 356/367 |
| 5,369,496 | * | 11/1994 | Alfano et al. ........................ 356/446 |
| 5,396,329 | * | 3/1995 | Kalawsky .............................. 356/364 |
| 5,404,225 | | 4/1995 | Bushman . |
| 5,424,536 | * | 6/1995 | Moriya ................................. 356/369 |
| 5,543,917 | | 8/1996 | Bushman . |
| 5,598,298 | | 1/1997 | Whitehead et al. . |
| 5,598,842 | * | 2/1997 | Ishihara et al. ........................ 356/39 |

OTHER PUBLICATIONS

Jacques, Polarized Light Transmission Through Skin Using Video Reflectometry, BiOS Conference, Jan. 27–Feb. 1, 1996, SPIE 2671–44, San Jose, CA, USA.

Demos, Optical Polarization Imaging Applied Optics, Jan. 1, 1997, vol. 36, No. 1, USA. (pp. 150–155).

* cited by examiner

Primary Examiner—Hoa Q. Pham
(74) Attorney, Agent, or Firm—Ingrid McTaggart

(57) ABSTRACT

A video imaging device includes a light source, a detector, and an optical polarization system for video imaging of superficial biological tissue layers. The device relies on taking a set of measurements at different polarization orientations so as to render a new image that is independent of the light reflected from the surface of a tissue sample and that is independent of the light scattered from deep tissue layers.

29 Claims, 4 Drawing Sheets

VIDEO IMAGING OF SUPERFICIAL BIOLOGICAL TISSUE LAYERS USING POLARIZED LIGHT

TECHNICAL FIELD

The present invention relates to a video camera whose images are based on polarized light to generate images from the first several hundreds of micrometers of superficial tissue layers below a tissue surface. This superficial region is where diseased tissue (pathology) usually arises in many tissues such as the skin, gastrointenstinal tract, lungs, reproductive tract, urinary tract, biliary tract, and inner lumen of blood vessels.

BACKGROUND OF THE INVENTION

The use of light in the ultraviolet-visible-near infrared wavelength range to image and characterize biological tissues is being widely pursued. These efforts have relied on several techniques. A first technique is absorption spectroscopy in which molecules electronically absorb certain wavelengths of light and hence attenuate the transmission or reflectance of that light to yield characteristic "absorption spectra". A second technique is Raman spectroscopy in which molecules vibrationally absorb certain wavelengths of light, more in the infrared, and hence attenuate transmission yielding "Raman spectra". A third technique is fluorescence spectroscopy in which molecules absorb certain wavelengths of light and re-emit longer wavelengths of fluorescence yielding characteristic "fluorescence spectra". A fourth technique is scattering spectroscopy, in which photons of different wavelengths are scattered differently by cells yielding "scattering spectra".

Motivated by a desire to better exploit scattering spectroscopy, this method of imaging concentrates the image contrast mechanism into the upper couple hundred micrometers of tissue. This superficial layer of tissue is the region where tissue pathology arises in many tissues.

One type of light used for imaging of materials is polarized light. Polarized light is strongly reflected off the surface of a material at the air/material interface. This reflectance depends on whether the polarized light is aligned "parallel" or "perpendicular" to the plane of the material. "Parallel" polarized light bounces off the material surface. "Perpendicular" polarized light penetrates into the material. This distinction between parallel and perpendicular alignment of polarized light is the basis of polarized lens in sunglasses which reject the parallel light reflected off a road surface.

Two approaches toward using this distinction between parallel and perpendicular light have been practiced. The first approach involves imaging material surfaces by selective acceptance of parallel polarized light. For example, polarized light has been used to detect "man-made" materials such as glass and metal within a field of "natural" materials such as trees, foliage, and organic soil. The second approach involves imaging material depths by selective rejection of parallel polarized light. For example, polarized light has been used to discriminate the skin surface from the skin depth. Illuminating the skin surface with parallel polarized light and viewing the skin by eye through glasses which are polarized parallel will emphasize the skin surface. Illuminating with parallel polarized light while viewing with glasses that are perpendicular polarized light will emphasize the tissue depth. In the latter case, there is always some parallel light which enters the skin but this light becomes randomly polarized by scattering within the tissue. Hence, viewing through perpendicular polarized glasses essentially rejects the surface reflectance and views the tissue depth with randomly polarized light. Imaging has been described that illuminates with perpendicular polarized light to achieve penetration of light into a tissue, then uses two wavelengths of light to enhance the contrast of a buried vessel based on absorption spectroscopy. Again, the image is based on light that penetrates deeply into the tissue and hence becomes randomly polarized. Viewing through an optical element which selects perpendicular polarized light offers a means of rejecting the glare of surface reflectance.

The task of identifying tissue pathology in the superficial tissue layers, however, is not served by either of the above. About 2–4% of the parallel polarized light is reflected by the surface. Such light does not interrogate the inner tissue where the pathology is located. About 91–93% of the reflected light is randomly polarized and is comprised of light that has penetrated deeply and been multiply scattered by the tissue. Such light is only a blinding artifact while attempting to observe the superficial tissues where pathology arises. Even observing the perpendicularly polarized light component of such multiply scattered deeply penetrating randomly polarized light does not discriminate light that scatters superficially from light that penetrated deeply. Only about 5% of the reflected light is not randomly polarized but is back-scattered by the superficial couple hundred micrometers of tissue. This invention provides a device to image based solely on that 5% of light that has penetrated the surface but not penetrated the tissue depth.

SUMMARY OF THE INVENTION

The present invention relies on taking a set of measurements using a broad illumination beam of light circularly polarized or linearly polarized at different angles of alignment and observing the tissue with a system that discriminates circularly polarized light and the various alignments of linearly polarized light. Also, a number of wavelengths of light are used to acquire images. The choice of wavelength may be made by the choice of light source or by including filters at either the source or camera detector. The wavelength dependence of polarized light scattering depends on the size distribution of tissue ultrastructure, i.e., cell membranes, protein aggregates, nuclei, collagen fibers, and/or keratin fibers. A set of images is taken with different combinations of source and collector polarization and wavelength. The images are then recombined to yield an image which rejects surface reflectance, rejects deeply penetrating light, and is optimally sensitive to just the light reflected from the superficial layer of the tissue.

The invention may include an optical element in contact with the tissue surface (e.g., a glass flat), an oblique angle of source illumination, and an angle of camera observation which differs from the angle of surface reflectance. The glass flat provides a tissue/glass interface that is well coupled and smooth such that oblique incidence of illumination light will cause surface reflectance to reflect at an oblique angle opposite the incident angle of illumination. The camera views the surface at an angle different from this angle of surface reflectance and hence no surface reflectance enters the camera.

For example, consider a system where linearly parallel polarized light is used for illumination and two images are acquired, one image selecting linearly parallel (Par) polarized light and one image selecting linearly perpendicular (Per) polarized light. The two images are recombined using the following expression:

$$\text{New image} = \text{Par} - \text{Per} \qquad \text{(Equation 1)}$$

Each Par and Per image includes about 90% of the corresponding parallel or perpendicular component of randomly polarzied light from deeper tissue layers and these component are equal in magnitude. Hence, the difference Par–Per subtracts these common contributions from deep tissue layers. The surface reflectance (or glare) is rejected by the strategy of oblique incidence of illumination and the optical element in contact with the tissue to ensure glare is diverted from the camera. Hence the Par–Per image is based on the 5% of the total reflected light which is back-scattered from only the superficial tissue layer.

Another example of how to recombine polarized light images to achieve optimal sensitivity to the scattering by the superficial tissue layer is to reject any interference due to superficial pigmentation that absorbs light. For example, a doctor cannot see the superficial tissue layer beneath a freckle or beneath (or within) a pigmented nevus. The following expression is useful:

New image=(Par–Per)/(Par+Per)   (Equation 2)

The numerator as before selects the light scattered from the superficial tissue layer. The denominator provides a means of rejecting the influence of a superficial layer of absorption such as the melanin in the epidermis of skin. Melanin is the absorbing pigment of skin. Such melanin acts as a filter on the tissue surface. All light must pass this filter twice, once on entry and once on exit. This filter attenuation is a common factor in all images acquired. Hence, by taking the ratio in Equation 2, the common factor cancels. In the image, the melanin disappears. For example, a pigmented freckle will disappear or the pigment of nevi will disappear. Hence, one can visualize the polarized light scattered from the superficial tissue layer without interference from superficial pigmentation.

The present invention has also found that using incoherent light, as opposed to coherent laser light, allows images which are free from "laser speckle" which is the interference of scattered coherent light. Such speckle is an interference that confuses the imaging of the superficial tissue layer. Lasers with very short coherence lengths (<<100 $\mu$m) qualify as an "incoherent" light source for such imaging.

Accordingly, an object of the present invention is to provide a video imaging device capable of generating an image using light scattered only by the superficial layer of a tissue.

Another object of the present invention is to provide a video imaging device capable of rejecting light reflected from the surface (surface glare).

Yet another object of the present invention is to provide a video imaging device capable of rejecting light reflected from deep tissue layers (randomly polarized light).

Still another object of the present invention is to provide a video imaging device capable of using oblique illumination through an optical element in contact with the tissue surface and light collection at an angle that avoids surface reflectance at the air/element interface in order to achieve the rejection of surface glare.

Another object of the present invention is to provide a video imaging device capable of acquiring a set of images based on different combinations of circularly and linearly polarized light for illumination and collection.

Another object of the present invention is to provide a video imaging device capable of acquiring a set of images based on different choices of wavelength of light for either illumination or collection.

Another object of the present invention is to provide a video imaging device capable of recombining the acquired set of images.

Another object of the present invention is to provide a video imaging device capable of recombining acquired images in order to cancel the influence of absorbing superficial pigmentation.

Another object of the present invention is to provide a video imaging device capable of using incoherent light (or low coherence light such as light having a coherence length <<100 $\mu$m) for illumination to avoid laser speckle in images.

DETAILED DESCRIPTION

Figure 1:
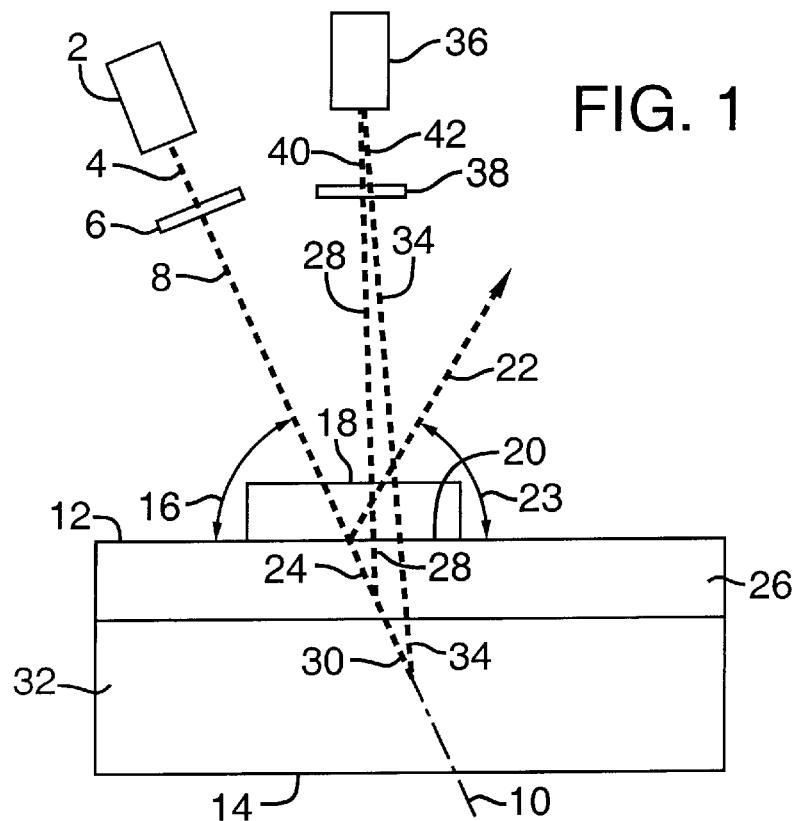
FIG. 1 is a schematic of the device of the present invention for use in topical imaging of the superficial layers of a tissue sample.

Referring to FIG. 1, a light source 2 is used to illuminate the tissue surface 12. The preferred light source is an incoherent light source or a low-incoherence light source (coherence length less than 100 $\mu$m) generating the illumination light 4. The light source 2 can generate light at one or more single wavelengths or bands of wavelengths either sequentially or simultaneously. The illumination light 4 passes through an optical element 6 which can filter or retard the light so as to modify the polarization of the transmitted light and/or can filter the light to pass a band of wavelengths. The preferred light source is an incoherent white light source such as a tungsten lamp. The optical element 6 is a combination of linear polarization filters and optical retarders, such as a quarter-wave plate or an electrically controlled thin-film liquid crystal retarder, which are aligned such that one of at least 7 types of polarized light are transmitted: randomly polarized light, horizontal or parallel or 90° linearly polarized light, vertical or perpendicular or 0° linearly polarized light, diagonal 45° linearly polarized light, diagonal −45° linearly polarized light, circularly left polarized light, and circularly right polarized light. All of these options are known descriptions of types of polarized light used in measuring the various elements of the Mueller matrix for describing how light transmits through a generic optical element which is well known in optics. It is believed that optical element 6 may also include a lens system. It is believed that optical element 6 can be implemented using holographic technology. The preferred embodiment of element 6 is a linear polarizer oriented parallel to the tissue surface 12.

The light 8 that has transmitted through element 6 follows a direction 10 and illuminates the surface 12 of the tissue 14 at an oblique angle 16. An optical element 18 in contact with the tissue provides good optical coupling to the tissue and a smooth element/tissue interface 20 which directs specularly reflected light 22 from the element/tissue interface away from the tissue at a new oblique angle 23. Such specularly reflected light 22 has not entered the tissue and has not interrogated the subsurface tissue layers and is not used for imaging in this invention. The light that is not specularly reflected and enters the tissue is denoted as 24. One portion 28 of the light 24 that enters the tissue is scattered by the superficial tissue layer 26. The remaining portion 30 of the light 24 penetrates deeply into the deeper tissue layer 32. The deeply penetrating light 30 is multiply scattered and becomes randomly polarized. A portion 34 of light 30 can scatter back up toward the camera system 36 but this light 34 is not used for imaging in this invention and will be rejected by subsequent algorithmic and arithmetic computations described later with regard to FIG. 2. The superficially scattered light 28 is used for imaging because its interaction with the superfical tissue layer 26 provides optical image contrast optimally localized in layer 26 which is the site where tissue pathology often arises. The light 28 scattered from layer 26 escapes the tissue and propagates toward the detection camera system 36. Both the light 28 and the light 34 pass through an optical element 38 before reaching the camera system 36. This optical element 38 is the same as optical element 6 in terms of the variety of types of polarized light and band of wavelengths that can be selected for transmission, which was described above for element 6. The choice of type of polarization for element 38 is independent of the choice of type of polarization for element 6. The preferred embodiment of optical element 38, which can be aligned in either a parallel or a perpendicular orientation, is a tunable liquid-crystal filter which can be electronically switched to pass different narrow bandwidths of light selected from the ultraviolet-visible-near infrared spectral range. The light 28 which transmits through element 38 is denoted 40 and the light 34 which transmits through element 38 is denoted 42. The light 40 and the light 42 reach the camera system 36 to form an image. The algorithmic and arithmetic combination of a set of images can yield a new image (referred to as reference numeral 56 in FIG. 2) which is based on light 40 and rejects light 42. The camera system 36 is described in FIG. 2. The light denoted as 4, 8, 22, 24, 30, 28, 34, 40, and 42 is illustrated as single dashed lines in FIG. 1 but the intention is to denote beams of light with some width and some degree of divergence or convergence.

Figure 2:
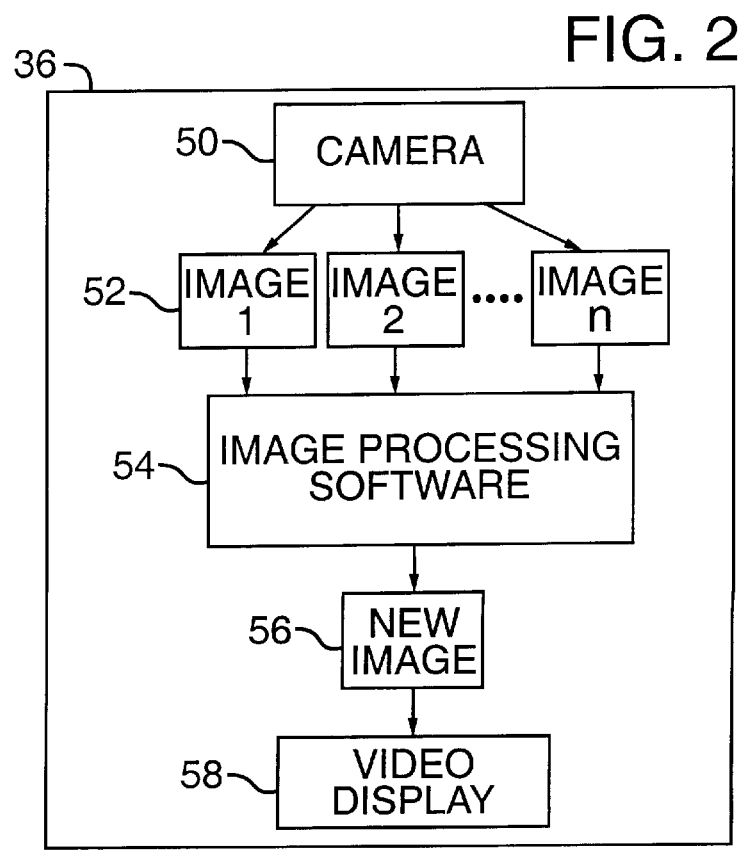
FIG. 2 is a flowchart of the process and calculations conducted by the device of the present invention.

Referring to FIG. 2, a flowchart describes the camera system 36 of FIG. 1 which consists of a camera 50 for detecting images, computer acquisition of a set of images 52, schematically depicted as images 1 to n where n is greater than one, each made with different combinations of polarization settings for optical elements 6 and 38 and/or selections of wavelength for the light source 2 or the filter function of optical element 6 or 38, image processing software 54 for algorithmic and arithmetic recombination of the image set 52 to yield a new image 56, which is displayed on a video display 58. The preferred embodiment would use two images in the image set 52: (1) a parallel image (Par) based on a selection of parallel linearly polarized light by element 6 and parallel linearly polarized light in element 38 in FIG. 1, and (2) a "perpendicular" image (Per) based on a selection of parallel linearly polarized light by element 6 and perpendicular linearly polarized light in element 38 in FIG. 1. This image set 52 is passed to the imaging process software 54 which computes pixel by pixel the following arithmetic combination of the two images: New image= (Par−Per)/(Par+Per), which is Equation 2 from above. This new image 56 is then displayed on a video display 58. Other choices of images for the image set 52 and for the arithmetic operations 54 to yield a new image 56 are desirable and easily implemented.

Figure 3:
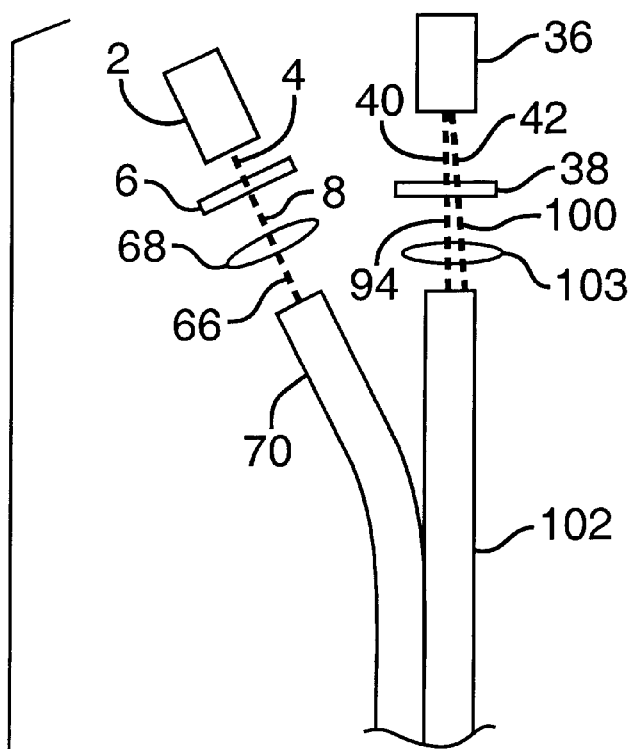
FIG. 3 is a schematic of the device of the present invention using an imaging fiber bundle for use in internal imaging of the superficial layers of a tissue sample wherein the fiber bundle is positioned generally perpendicularly to a tissue surface.
Figure 3:
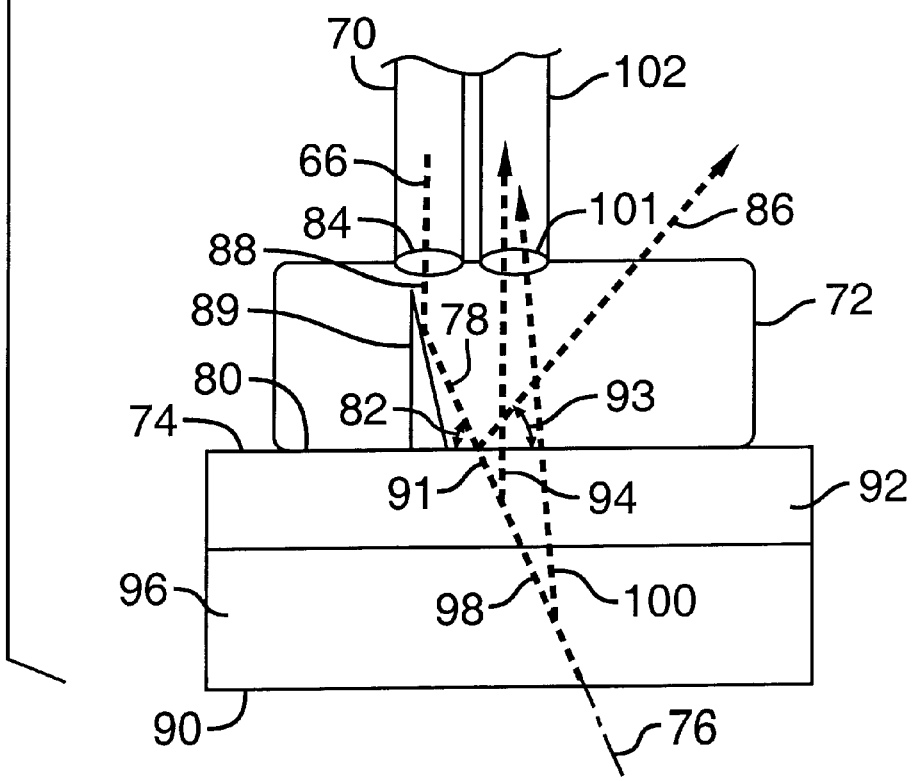

In FIG. 3, an alternative embodiment is shown which is appropriate for endoscopic and laparoscopic applications. The light source 2 delivers light 4 which passes through an optical element 6 which is identical to element 6 in FIG. 1 and transmits a type of light 8 that has a selected type of polarization. Either the source 2 or the element 6 may have a selected choice of wavelength band or bands. The transmitted light 8 is coupled by a coupling system 68, which may be a single lens or a lens assembly or some combination of lenses and mirrors or holographic device, into an optical fiber device 70 which is constructed with one or more optical fibers which are polarization-maintaining optical fibers that are common and commercially available. The light 8 that is coupled by coupling system 68 into fiber bundle 70 is denoted as 66 and is delivered by fiber bundle 70 to an optical element 72 in contact with the tissue surface 74.

The element 72 consists of a means of directing illumination light 66 into a new direction 76 and the light in this new direction is denoted as 78 which obliquely illuminates the element/tissue interface 80 at an angle 82. Element 72 may include an optical lens 84 to focus the light 66 from the fiber device 70 to yield light 88 which is deflected by a mirror 89 to yield light 78 at the desired direction 76 for illuminating the element/tissue surface 80. It is believed that other embodiments using lens, mirrors and/or holographic devices can achieve the same purposes served by element 72 and its associated components 84 and 89 which are to obliquely deliver illumination light 66 along the direction 76 to the element/tissue interface 78 at angle 82. The optical element 72 establishes an element/tissue interface 80 which specularly reflects light 86 at a new angle 93 and light 86 does not enter the tissue and is not used for imaging. The light not specularly reflected as 86 is denoted as 91 and enters the tissue. A portion of light 91 scatters from the superficial tissue layer 92 back toward the camera system 36 to yield scattered light 94 that is used for imaging. A portion of light 91 penetrates into the deeper tissue layer 96 and is denoted as 98 and becomes randomly polarized. A portion of light 98 is scattered back toward the camera system 36 and this portion is denoted as 100. Light 100 is not used for imaging. The scattered light 94 and 100 are coupled by the optical element 101 into a second optical fiber bundle device 102. The fiber bundle device 102 is an imaging optical fiber bundle composed of polarization-maintaining fibers which map the image entering the bundle to the an identical image exiting the bundle. Imaging optical fiber bundles are commercially available and can be implemented using polarization-maintaining optical fibers.

The optical element 101 may consist of a single lens, a lens assembly, or a holgraphic device in order to achieve proper focusing and coupling of the image from the scattered light 94 and 100 into the fiber bundle 102. The image based on the scattered light 94 and 100 is carried by the fiber bundle 102 to a lens assembly 103 that focuses the light from fiber bundle 102 through an optical element 38 onto the camera system 36 to form an image. The optical element 38 which is the same as element 38 in FIG. 1 and selects one type of polarization for transmission. The light 94 that passes through element 38 has been filtered or retarded and is denoted as 40, as in FIG. 1. The light 100 that passes through element 38 has been filtered or retarded and is denoted as 42, as in FIG. 1. The amounts of light 40 and 42 that reach the camera system 36 depends on the choices of wavelength for the light source 2 or for the optical elements 6 and 38 and on the choices of types of polarization for optical elements 6 and 38. The algorithmic and arithmetic combination of a set of images can yield a new image (referred to as reference numeral 56 in FIG. 2) which is based on light 40 and rejects light 42. The camera system 36 was described in FIG. 2.

Figure 4:
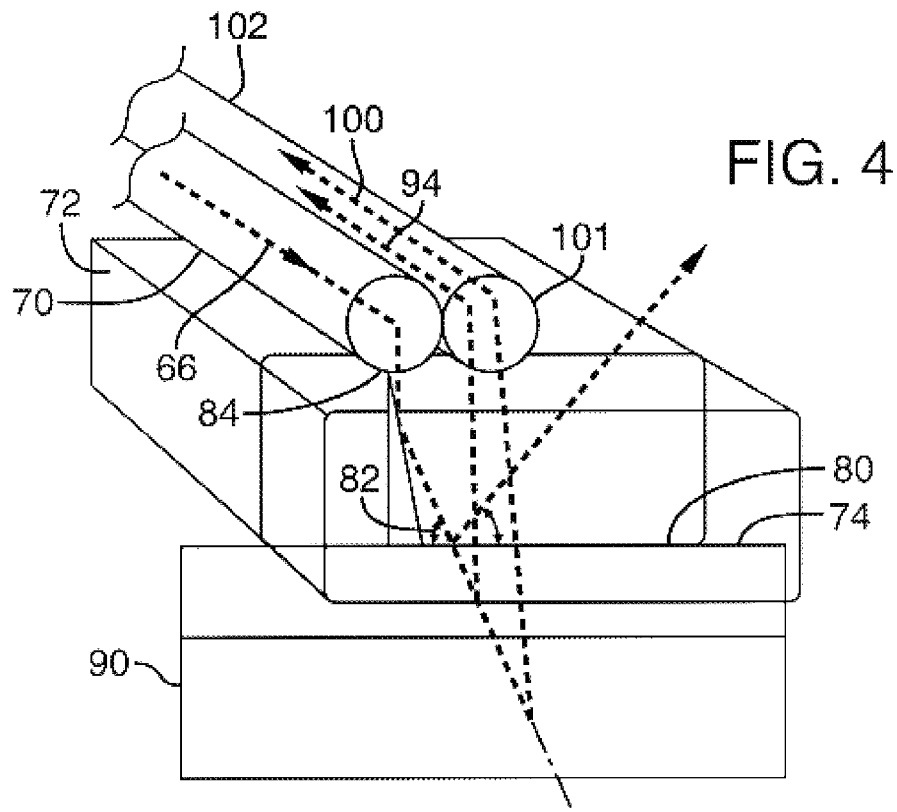
FIG. 4 is a schematic of the device of the present invention using an imaging fiber bundle for use in internal imaging of the superficial layers of a tissue sample wherein the fiber bundle is positioned generally parallel to a tissue surface.

FIG. 4 shows a system identical to FIG. 3 however the orientation of the fiber bundle devices 70 and 102 are oriented parallel to the tissue surface 74 and optical element 72. All aspects of FIG. 4 have the same labeling as in FIG. 3. The figure is drawn with a three-dimensional aspect to illustrate the parallel orientation of fiber bundles 70 and 102, however the drawing is schematic in nature and the tissue 90 is shown two-dimensionally, exactly as in FIG. 3. The coupling system 84 accomplishes the task of redirecting the illumination light 66 down onto the issue/element interface 80 at an oblique angle 82, as in FIG. 3, coupling system 101 collects light 94 and 100 for return to the camera system (referred to as reference number 36 in FIG. 2). Such a configuration (fiber bundles 70 and 102 parallel to tissue surface 74 and optical element 72) is important when requiring side viewing of a tissue surface while the total system is inserted into narrow internal spaces of the body. FIG. 4 is in contrast to FIG. 3 which showed the fiber bundle devices 70 and 102 to be oriented perpendicular to the tissue surface 74 and optical element 72. Such perpendicular configuration is often important when viewing a tissue surface for example when viewing the skin, the oral cavity, the stomach, and other surfaces best viewed from a perpendicular orientation.

Figure 5A:
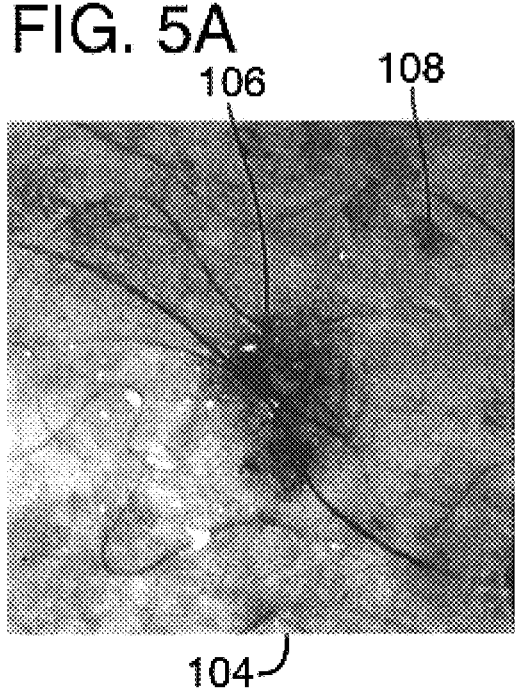
FIG. 5A is an image of a freckle seen with the naked eye.
Figure 5B:
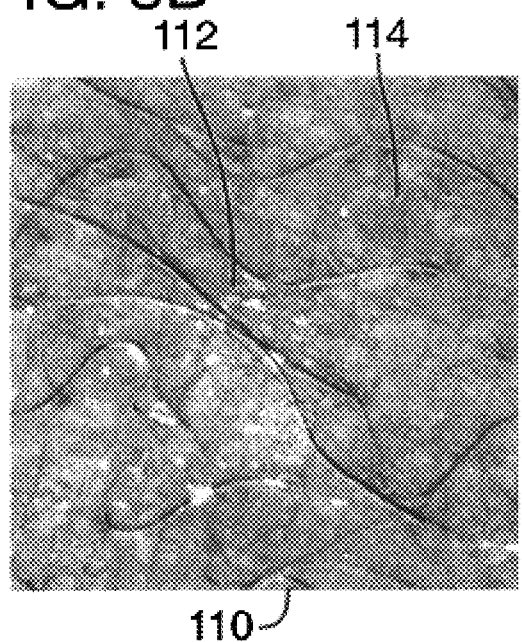
FIG. 5B is an image of the freckle of FIG. 5A as created by the device of the present invention.

FIG. 5A shows an image 104 of a freckle 106 on the skin 108 using randomly polarized light. FIG. 5B shows an image 110 of a freckle 112 on the skin 114 using the preferred embodiment described in FIG. 2. FIGS. 5A and 5B show images of the exact same skin site. The melanin pigment of the freckle 112 appears to disappear in image 110 and shows nothing abnormal underlying the freckle.

Figure 6A:
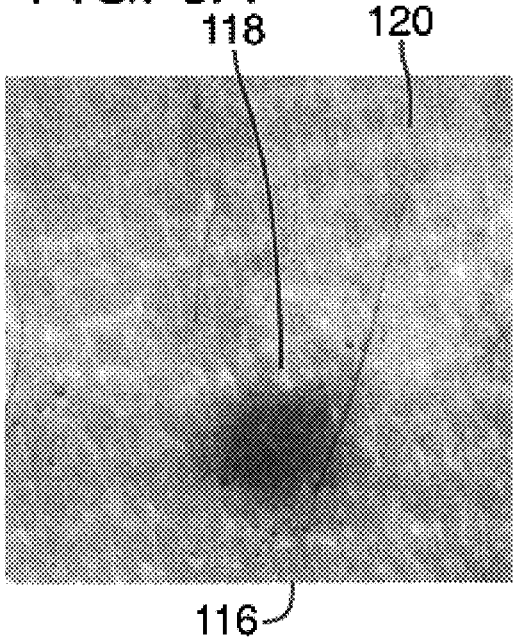
FIG. 6A is an image of a nevus seen with the naked eye.
Figure 6B:
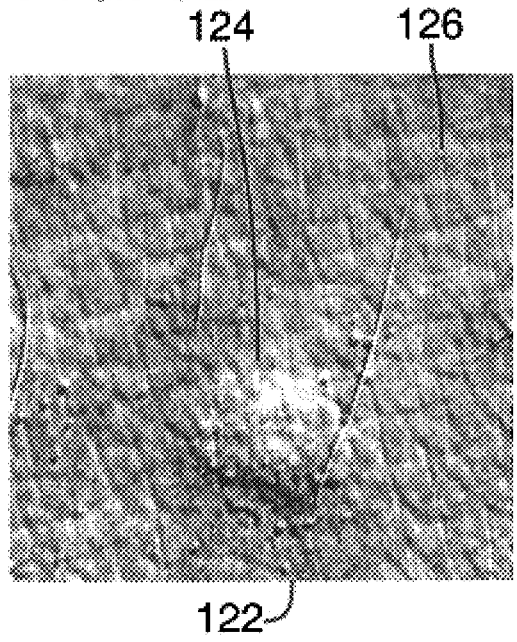
FIG. 6B is an image of the nevus of FIG. 6A as created by the device of the present invention.

FIG. 6A shows an image 116 of a pigmented nevus 118 on the skin 120 using randomly polarized light. FIG. 6B shows an image 122 of a pigmented nevus 124 on the skin 126 using the preferred embodiment described in FIG. 2. The melanin pigment of the nevus 124 appears to disappear in image 122 and reveals a distinctive tissue structure in the superficial tissue layer. A doctor's eye cannot see the structure shown in image 122.

Figure 7:
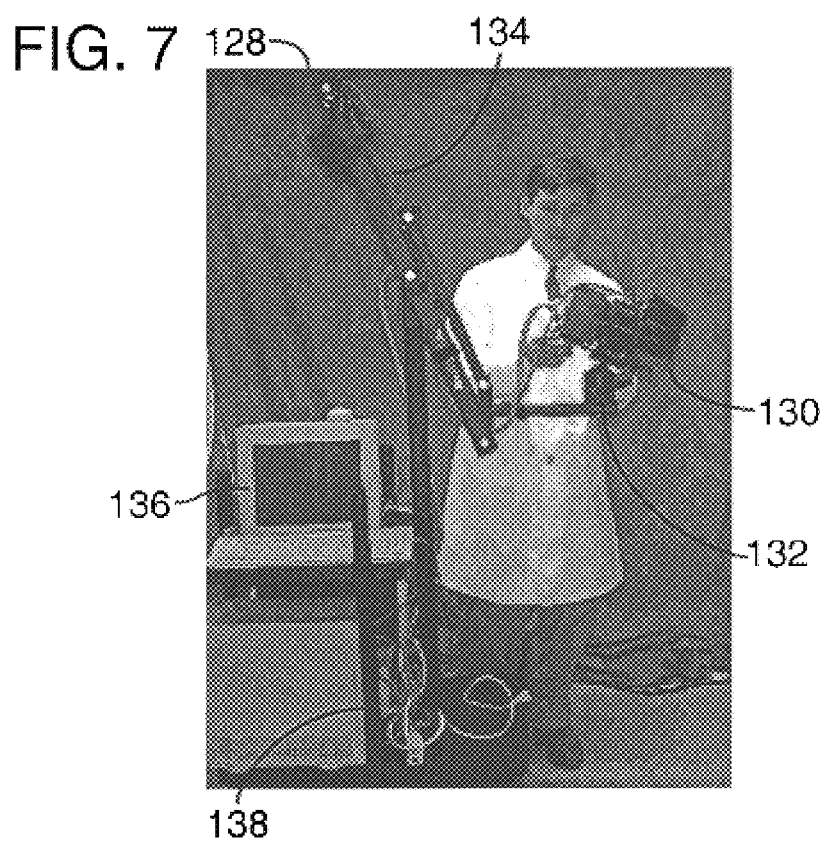
FIG. 7 is a photograph of a clinical prototype of the device of the present invention.

FIG. 7 shows a clinical prototype 128 which was prepared and tested in a pilot clinical trial. The entire light source and camera assembly as described in FIG. 1 is denoted as 130 which is held on a universal joint 132 supported by a counter-balanced levered arm 134. The entire system (130, 132, 134) along with the computer data acquisition and display system 136 is placed on a cart 138 which allows the prototype 128 to be mobile in the clinic.

I claim:

1. An imaging device for imaging light scattered by a tissue, comprising:
   a light source for emitting light along a light path to a living tissue sample including a surface, a deep tissue layer and a superficial tissue layer positioned therebetween wherein said light source emits a first light emission along said light path and emits a second light emission along said light path;
   an optical assembly positioned within said light path for modifying a characteristic of the light passing through said optical assembly; and
   a detector for detecting a first light detection scattered by the superficial and the deep tissue layers along said light path which corresponds to said first light emission, and for detecting a second light detection scattered by the superficial and the deep tissue layers along said light path which corresponds to said second light emission, said detector being positioned with respect to said light source such that light emitted by said light source and reflected by said surface is not detected by the detector and, said detector conducting arithmetic manipulation of said first light detection and said second light detection scattered by said superficial tissue layer and said deep tissue layer for producing an image comprised exclusively of light scattered by said superficial tissue layer.

2. An imaging device according to claim 1 wherein said optical assembly includes an optical element positioned within said light path between said light source and said surface.

3. An imaging device according to claim 1 wherein said optical assembly includes an optical element positioned within said light path between said surface and said detector.

4. An imaging device according to claim 1 wherein the light source emits incoherent light.

5. An imaging device according to claim 4 wherein the incoherent light has a coherence length of less than 100 $\mu$m.

6. An imaging device according to claim 1 wherein the light source is capable of emitting light sequentially or simultaneously at one or more wavelengths or bands of wavelengths.

7. An imaging device according to claim 1 wherein the optical assembly includes a combination of a linear polarization filter and an optical retarder.

8. An imaging device according to claim 7 wherein the polarization filter is a quarter-wave plate and the optical retarder is an electrically controlled thin-film liquid crystal retarder.

9. An imaging device according to claim 1 wherein the optical assembly includes a wavelength filter that selectively allows a distinctive band of wavelengths to pass therethrough.

10. An imaging device according to claim 1 wherein light reflected by the surface defines an angle of surface reflectance with respect to said surface, the light path between the surface and the detector defines a detection angle, and wherein said angle of surface reflectance is different than said detection angle.

11. An imaging device according to claim 1 further comprising an optical coupling element positioned in contact with the surface to define a smooth optical coupling element/tissue interface.

12. An imaging device according to claim 1 wherein the detector includes a camera system.

13. An imaging device according to claim 1 wherein the detector includes a computer for conducting the arithmetic manipulation of light for producing said image.

14. An imaging device according to claim 1 further comprising an optical fiber device positioned within said light path for imaging a superficial layer of an internal tissue.

15. An imaging device according to claim 14 wherein the optical fiber device comprises at least one polarization maintaining optical fiber operatively connected to said light source and said detector.

16. An imaging device according to claim 1 wherein said first light detection and said second light detection each comprise a distinctive band of wavelengths.

17. An imaging device according to claim 1 wherein said first light detection and said second light detection each comprise a distinctive polarization and wherein said arithmetic manipulation comprises subtracting said first light detection from said second light detection.

18. An imaging device according to claim 1 wherein said first and second light emissions comprise linearly parallel polarized light, said first light detection comprises linearly parallel polarized light, and said second light detection comprises linearly perpendicular polarized light.

19. An imaging device according to claim 1 wherein said optical assembly comprises a first optical polarizer positioned between said light source and said surface and a second optical polarizer positioned between said surface and said detector.

20. An imaging device according to claim 1 wherein light scattered by said superficial tissue layer undergoes a single scattering event and wherein light scattered by said deep tissue layer undergoes multiple scattering events.

21. An imaging device according to claim 1 wherein said superficial tissue layer comprises the first 200 micrometers of tissue below the surface.

22. An imaging device according to claim 1 further comprising an optical redirection device positioned within the light path between said light source and said surface for redirecting light emitted from the light source toward said surface such that the detector does not detect light reflected from said surface.

23. An imaging apparatus for detecting light scattered by a tissue, comprising:
   a light source for emitting light along a source light path to a tissue including a surface, a deep tissue layer and a superficial tissue layer positioned therebetween;
   a detector for detecting light scattered by the superficial and the deep tissue layers along a detector light path;
   an optical polarization system positioned within the detector light path for modifying a polarization of the light scattered by said tissue and detected by the detector,
   wherein said detector is positioned relative to said light source such that light scattered by the surface of the tissue is not detected by the detector and wherein said detector includes a light recombination device that conducts arithmetic manipulation of the light transmitted by the optical polarization system to produce an image comprised exclusively of the light scattered from said superficial tissue layer.

24. A method of producing an image of light scattered exclusively from an upper layer of a tissue, comprising the steps of:
   emitting first and second light emissions toward a living tissue including a surface, a lower tissue layer, and an upper tissue layer positioned therebetween;
   detecting first and second light detections scattered from said upper and lower tissue layers while rejecting light reflected from said surface of the tissue wherein said first light detection corresponds to said first light emission and said second light detection corresponds to said second light emission; and
   conducting mathematical manipulation of the first and second light detections scattered from said upper and lower tissue layers to produce an image comprised exclusively of light scattered from said upper tissue layer.

25. The method of claim 24 further comprising placing an optical assembly between the tissue and the detector wherein said optical assembly changes a characteristic of the light as it passes through the optical assembly.

26. The method of claim 25 wherein the optical assembly comprises a polarization filter.

27. The method of claim 25 wherein the optical assembly comprises a wavelength filter.

28. The method of claim 24 further comprising positioning an optical fiber within a light path of the light emitted from the light source to the tissue.

29. The method of claim 24 wherein said upper tissue layer comprises the first 200 micrometers of tissue below the surface.

* * * * *